(12) United States Patent
Chattaraj et al.

(10) Patent No.: US 9,622,981 B2
(45) Date of Patent: Apr. 18, 2017

(54) LIQUID-FILLED HARD GEL CAPSULE PHARMACEUTICAL FORMULATIONS

(75) Inventors: Sarat C. Chattaraj, Morgantown, WV (US); Glenn Allen Redelman, Morgantown, WV (US)

(73) Assignee: Mylan Inc., Canonsburg, PA (US)

( * ) Notice: Subject to any disclaimer, the term of this patent is extended or adjusted under 35 U.S.C. 154(b) by 42 days.

(21) Appl. No.: 13/617,714

(22) Filed: Sep. 14, 2012

(65) Prior Publication Data
US 2013/0129822 A1 May 23, 2013

Related U.S. Application Data

(60) Provisional application No. 61/560,939, filed on Nov. 17, 2011.

(51) Int. Cl.
| | |
|---|---|
| *A61K 9/48* | (2006.01) |
| *A61K 31/473* | (2006.01) |
| *A61K 47/14* | (2017.01) |
| *A61K 47/44* | (2017.01) |
| *A61K 31/18* | (2006.01) |

(52) U.S. Cl.
CPC .......... *A61K 9/4858* (2013.01); *A61K 9/4808* (2013.01); *A61K 9/4825* (2013.01); *A61K 9/4875* (2013.01); *A61K 31/18* (2013.01); *A61K 31/473* (2013.01); *A61K 47/14* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,565,467 A | 10/1996 | Batchelor et al. | |
| 5,846,976 A | 12/1998 | Batchelor et al. | |
| 5,998,427 A | 12/1999 | Batchelor et al. | |
| 2003/0077297 A1* | 4/2003 | Chen et al. | 424/400 |
| 2003/0124182 A1 | 7/2003 | Shojaei et al. | |
| 2003/0232078 A1 | 12/2003 | Dong et al. | |
| 2003/0235595 A1 | 12/2003 | Chen et al. | |
| 2006/0003002 A1 | 1/2006 | Fikstad et al. | |
| 2010/0173882 A1 | 7/2010 | Giliyar et al. | |

FOREIGN PATENT DOCUMENTS

| | | |
|---|---|---|
| WO | 2006055659 A2 | 5/2006 |
| WO | WO 2006055659 A2 * | 5/2006 |
| WO | 2010092596 A1 | 8/2010 |
| WO | WO 2010092596 A1 * | 8/2010 |
| WO | 2011004395 A1 | 1/2011 |

OTHER PUBLICATIONS

International Search Report and Written Opinion dated Dec. 11, 2012 pertaining to PCT/US2012/057927.
Cole E.T., "Liquid filled and sealed hard gelatin capsules," Gattefossé Bulletin, 92, 1999, reprinted.
Svensson, A. et al, "Hydration of an amphiphilic excipient, Gelucire 44/14," HAL Id: hal-00015990, available at: https://hal.archives-ouvertes.fr/hal-000159990, Dec. 15, 2005.

* cited by examiner

*Primary Examiner* — Rachael E Bredefeld
*Assistant Examiner* — Dominic Lazaro

(57) ABSTRACT

Embodiments of liquid-filled hard gel capsule pharmaceutical formulations comprise a non-emulsified mixture, wherein the non-emulsified mixture comprises about 0.1 to about 5% by weight of at least one active pharmaceutical ingredient, about 50 to about 95% by weight medium chain triglycerides, and about 5 to about 25% by weight medium chain mono/diglycerides, wherein the medium chain triglycerides and medium chain mono/diglycerides are present at a ratio by weight of from about 10:1 to about 5:1.

11 Claims, No Drawings

LIQUID-FILLED HARD GEL CAPSULE PHARMACEUTICAL FORMULATIONS

CROSS-REFERENCE TO RELATED APPLICATIONS

This application claims the benefit of U.S. Provisional Application Ser. No. 61/560,939 filed Nov. 17, 2011.

TECHNICAL FIELD

Embodiments of the present invention are generally directed to liquid-filled hard gel capsule formulations, and in specific embodiments, are directed to liquid-filled hard gel capsule formulations comprising dutasteride.

BACKGROUND

Dutasteride, a synthetic 4-azasteroid compound, is an antiandrogen with the chemical name (5α,17β)-N-[2,5 bis (trifluoromethyl)phenyl]-3-oxo-4-azaandrost-1-ene-17-carboxamide. Dutasteride is indicated for the treatment of symptomatic benign prostate hyperplasia (BPH) in men with enlarged prostate glands. Dutasteride, a synthetic 4-azasteroid compound is a selective inhibitor of the type 1 and type 2 isoforms of steroid 5α-reductase, an intracellular enzyme that converts testosterone to 5α-dihydrotestosterone. The empirical formula of Dutasteride is $C_{27}H_{30}F_6N_2O_2$. Dutasteride is a white to off-white colored powder and stable under ordinary conditions. The melting point is 245° C.-245.5° C. Dutasteride is soluble in ethanol (44 mg/mL), methanol (64 mg/mL), and polyethylene glycol 400 (3 mg/mL), but it is insoluble in water. Dutasteride has a partition coefficient, Log P=5.609±0.618.

Commercially available soft gel capsule formulations (e.g., Avodart®, which is produced by Glaxo Smithkline Pharmaceuticals), is a soft gelatin capsule used in the treatment of BPH, which contains 0.5 mg dutasteride dissolved in a mixture of mono/diglycerides of caprylic/capric acid (Capmul MCM) (349.5 mg) and butylated hydroxytoluene (0.035 mg). However, the manufacture of soft gel capsules is a slow and burdensome process, and therefore the manufacture of soft gel capsules is cost intensive and inefficient.

Consequently, there is a need for improved hard gel capsule formulations that reduce manufacturing costs, while maintaining the bioavailability and stability of the soft gel dosage forms.

SUMMARY

According to one embodiment, a liquid-filled hard gel capsule pharmaceutical formulation is provided. The liquid-filled hard gel capsule formulation comprises a non-emulsified mixture disposed in a hard capsule shell, wherein the non-emulsified mixture comprises about 0.1 to about 5% by weight of at least one active pharmaceutical ingredient, about 50 to about 95% by weight medium chain triglycerides, and about 5 to about 25% by weight medium chain mono/diglycerides, wherein the medium chain triglycerides and medium chain mono/diglycerides are present at a ratio by weight of from about 10:1 to about 5:1.

According to another embodiment, another liquid-filled hard gel capsule pharmaceutical formulation is provided. The liquid-filled hard gel capsule pharmaceutical formulation comprises a non-emulsified mixture disposed in a hard capsule shell, wherein the non-emulsified mixture comprises about 0.1 to about 5% by weight of at least one active pharmaceutical ingredient; about 50 to about 95% by weight long chain triglycerides; and about 5 to about 25% by weight medium chain mono/diglycerides, wherein the long chain triglycerides and medium chain mono/diglycerides are present at a ratio by weight of from about 10:1 to about 5:1.

These and additional features provided by the embodiments of the present invention will be more fully understood in view of the following detailed description.

DETAILED DESCRIPTION

Embodiments of the present invention are directed to improved liquid-filled hard gel capsule formulations comprising an active ingredient (e.g., dutasteride) in a non-emulsified mixture disposed in a capsule, for example, a hard gelatin capsule. As used herein, "liquid-filled hard gel capsules" refer to capsule formulations wherein the liquid pharmaceutical is filled into solid capsule shells, which do not require drying, whereas "soft gel capsules" include a liquid gelatin coating solution that requires significant drying. That being said, while the capsule shells of the liquid-filled hard gel capsules do not require drying, a liquid banding solution may be applied to the hard gel capsules, which may require some level of drying albeit minimal as familiar to one of ordinary skill in the art.

Without being bound by theory, the hard shell may provide some desirable advantages over the soft shell. For example, the soft gel shell may include a higher water content, which may be undesirable for moisture sensitive products. Moreover, soft liquid-filled gel capsules may also contain plasticizers (for example, glycerol or sorbitol) which can migrate into the capsule and possible react/crosslink with other ingredients of the pharmaceutical formulation. In contrast, the gelatin used in hard capsule shells is substantially free of plasticizer. Moreover, hard shell capsules tend to be more thermally stable. Additionally, manufacturing of soft gelatin capsule takes a longer time compared to liquid filled and banded two piece hard gelatin capsule dosage forms. For example, soft gel capsules require tray drying at room temperature, which can result in a drying period of 3-7 days, whereas hard gel capsules do not require a drying process. They are merely filled with the liquid pharmaceutical ingredient, and sealed with a banding solution.

In one embodiment, the non-emulsified mixture comprises at least one active pharmaceutical ingredient, medium chain triglycerides, and medium chain mono/diglycerides, wherein the medium chain triglycerides and medium chain mono/diglycerides are present at a ratio by weight of from about 10:1 to about 5:1. As described below, the combination of medium chain triglycerides and the medium chain mono/diglycerides effectively solubilizes the active ingredient (e.g., dutasteride), while maintaining the bioavailability.

As used herein, "non-emulsified mixture" means a mixture that is not a colloidal or multiphase mixture, and does not include emulsifying surfactants that may produce a multiphase mixture. Specifically, the pharmaceutical formulation is substantially free of surfactants having a hydrophilic-lipophilic balance (HLB) of greater than or equal to 8. As used herein "substantially free" means less than 0.5% by weight, or less than 0.1% by weight, or 0%. In an exemplary embodiment, the non-emulsified mixture is a substantially homogenous mixture.

Active Pharmaceutical Ingredient

Regarding the active pharmaceutical ingredient, various suitable active ingredients are contemplated herein. In one embodiment, the active ingredient comprises dutasteride. In yet another embodiment, a combination of the active ingredients is used, for example, dutasteride and tamsulosin. Dutasteride and tamsulosin are co-administered in the FDA approved drug Jalyn® produced by Glaxo SmithKline. In alternative embodiments, the pharmaceutical formulations of the invention can be used in a combination therapy with other therapeutic agents delivered in a separate pharmaceutical formulation or delivery vehicle. In yet another embodiment, the pharmaceutical formulation of the present invention may be administered prior or subsequent to administration of another pharmaceutical formulation.

While the present examples focus primarily on dutasteride in a capsule, various other pharmaceutical active ingredients are contemplated herein, for example, acamprosate, acebutolol, acitretin, alprazolam, alfaxalone, amlodipine, amiodarone, amoxicillin, amprenavir, anagrelide, anastrazole, atenolol, atovaquone, atorvastatin, avasimibe, azathioprine, azithromycin, bacampicillin, beclomethasone, betaxolol, bicalutamide, bisoprolol, bosentan, bucindolol, budesonide, buproprion, calcitriol, carvedilol, candesartan cilexetil, carbamezepine, carbidopa, celecoxib, cetirizine, chenodeoxycholic acid, ciclesonide, cilostazol, cinnarizine, ciprofloxacin, citalopram, clarithromycin, clobetasol, clonazepam, clopidogrel, clorazepate dipotassium, clozapine, cyclosporine, dehydroepiandrosterone, dehydroepiandrosterone sulfate, delaviridine mesylate, desogestrel, dihydroergotamine, dianabol, didanosine, dilevalol, dipyridamole, docetaxel, donezepil, desloratadine, dronobinol, econazole, efivarenz, enlopitant, entacapone, eplerenone, eprosartan, ergotamine, esmolol, estazolam, etoprolol, etoricoxib, everolimus, ezetimibe, exemestane, fenofibate, fexofenadine, finasteride, fluconazole, fluphenazine, fluoxetine, frovatriptan, gangciclovir, galantamine, granisetron, griseofulvin, hydrocodone, indinavir, irbesartan, isradipine, itasetron, itraconazole, ketoconazole, labetalol, lamivudine, lamotrigine, lansoprazole, lercanidipine, letrozole, levadopa, levofloxacin, loratadine, lorazepam, lovastatin, mefloquin, megestrol, megestrol acetate, meloxicam, memantine, metaxolone, methylphenidate, metolazone, mifepristone, mirtazapine, modafinil, morphine, mometasone, nadalol, nefazodone, nelfinavir, nevibulol, nevirapine, nifedipine, nefinavir, nimodipine, nisoldipine, norethindrone, norethindrone acetate, norfloxacin, nortestosterone, olanzapine, olmesartan medoxomil, ondasetron, oxacarbezapine, oxaprozin, oxprenolol, paroxetine, pemoline, penicillin, pergolide, phenazopyridine, pioglitazone, pimecrolimus, pitavastatin, pregnanediol, pregnanolone, pregnenolone, allopregnanolone, epiallopregnanolone, progesterone, propafenone, propanolol, quetiapine, raloxifene, ramipril, ranolazine, rifapentin, risperidone, ritonavir, rivastigmine, rofeconxib, ropinorole, rosiglitazone, rosuvastatin, salmeterol, saquinavir, sertraline, sildenafil, sirolimus, sotalol, simvastatin, sparfloxacin, spironolactone, squanavir mesylate, stavudine, sulfamethoxazole, sulpride, sumatriptan, tacrolimus, tadalafil, tegaserod, telmisartan, tenovir, terbinafine, terconazole, testosterone and testosterone esters, testosterone undecanoate, methyltestosterone, thalidoamide, tiagabine, tibolone, tizanidine, tolcapone, topiramate, torcetrapib, trandolapril, tramadol, triazolam, trimethoprim, valdecoxib, vardenafil, valsartan, valrubicin, ursodeoxycholic acid, voriconazole, zafirlukast, zalcitabine, zalepelon, zanamvir, zileuton, ziprasidone, Zidovudin and zolpidem.

Various amounts of the pharmaceutical active ingredients are contemplated herein. In one or more embodiments, about 0.1 to about 5% by weight of at least one active pharmaceutical ingredient, or about 0.1 to about 1% by weight of at least one active pharmaceutical ingredient (e.g., dutasteride) are included. If dutasteride is utilized as the active pharmaceutical ingredient, the pharmaceutical formulation may include up to 1 mg of the dutasteride, or about 0.5 mg of the dutasteride.

Medium Chain Triglycerides

As used herein, "medium chain triglycerides" means C6-C12 ester chains formed via the esterification of glycerol with three fatty acids. There are various sources of medium chain triglycerides, for example coconut oil, palm kernel oils, etc. Fractionated coconut oils are the most commonly used sources for medium chain triglycerides. Examples of commercially available medium chain triglycerides may include Miglyol® 810, 812 or 881 produced by Sasol Germany GMBH, Captex® 300, 355, or 810D produced by the Abitec Corporation, Neobee® M5 by the Stepan Company, Crodamol® GTC/C produced by Croda Inc, and Labrafac® Lipophile WL 1349 produced by the Gattesfosse Group. In one exemplary embodiment, the medium chain triglyceride may comprise Captex® 355, which is a triglyceride of caprylic (C8)/capric (C10) acid.

Various amounts of the medium chain triglycerides may be included in the pharmaceutical formulation. In one or more embodiments, the pharmaceutical formulation may comprise about 50 to about 95% by weight medium chain triglycerides, or about 85 to about 95% by weight medium chain triglycerides. Moreover, in exemplary embodiments, the pharmaceutical formulation may include from about 100 to about 300 mg, or from about 200 to 300 mg of the weight medium chain triglycerides, or about 225 to 275 mg of the weight medium chain triglycerides, or about 250 mg of the weight medium chain triglycerides.

Medium Chain Mono/Diglycerides

Similar to medium chain triglycerides, "medium chain monoglycerides" and "medium chain diglycerides" are C6-C12 ester chains formed via the esterification of glycerol with one fatty acid or two fatty acids, respectively. Examples of commercially available medium chain mono/diglycerides may include the Capmul® products produced by Abitec. It is also contemplated to use medium chain mono/diglyceride compounds that also include medium chain triglycerides, for example, the commercially available Imwitor® compositions produced by Sasol.

In exemplary embodiments, the medium chain mono/diglycerides may comprise Capmul® MCM, which include medium chain mono/diglycerides of caprylic (C8)/capric (C10) acid. While all grades of the Capmul® MCM product line are suitable for use in the present invention, e.g., national formulary (NF) grade or Capmul MCM® EP, it may be desirable to use to EP grade as it includes 3% glycerol, whereas the NF grade includes 7% glycerol.

In accordance with one or more embodiment, the pharmaceutical formulation may comprise about 5 to about 25% by weight medium chain mono/diglycerides, or from about 5 to about 15% by weight medium chain mono/diglycerides. Moreover, in exemplary embodiments, the pharmaceutical formulation may include about 20 to 50 mg of the weight medium chain mono/diglycerides, or about 25 to 30 mg of the weight medium chain mono/diglycerides, or about 25 mg of the weight medium chain mono/diglycerides.

Without being bound by theory, the mixture of medium chain triglycerides and medium chain mono/diglycerides is important for the bioavailability of the active ingredient inside the liquid-filled hard gel capsule formulation. While a soft gel capsule may only include medium chain mono/diglycerides, a hard gelatin capsule with only medium chain mono/diglycerides may not provide the requisite physical stability of the finished dosage forms. However, a mixture of medium chain triglycerides and medium chain mono/diglycerides inside a hard gelatin capsule may achieve the desired product stability, solubility and bioavailability of the active pharmaceutical ingredient. Consequently, in accordance with the present invention, the ratio by weight of the medium chain triglycerides to the medium chain mono/diglycerides facilitates the solubility and stability of the active pharmaceutical ingredient (for example, dutasteride) within the non-emulsified mixture prior to and after the addition of the mixture into the capsule. The medium chain triglycerides and medium chain mono/diglycerides may be present at a ratio by weight of from about 10:1 to about 5:1, or from about 10:1 to about 7:1.

Antioxidant

The pharmaceutical formulation may further comprise at least one antioxidant. The antioxidant used in the oral composition of the present invention may be selected from butylated hydroxytoluene, butylated hydroxyl anisole, α-tocopherol ascorbic acid, ascorbyl palmitate sodium ascorbate, vitamin E, tartaric acid and the like. In one embodiment, the antioxidant comprises butylated hydroxytoluene (BHT). Various amounts for the pharmaceutical formulation are contemplated herein. For example, the pharmaceutical formulation may comprise about 0.1 to about 1% by weight of the antioxidant, or about 0.1 to about 0.2 by weight of the antioxidant.

Optional Excipients

In addition to the above components, the present inventions may include various other excipients familiar to one or ordinary skill in the art. For example, the excipients used in the oral composition of the present invention may be selected from diluents, binders, lubricants, disintegrants, flavoring agents, coloring agents, stabilizers, glidants, plasticizers, preservatives and sweeteners.

Diluents may include liquid diluents such as any long chain triglyceride (arachis oil, almond oil, peanut oil, palm oil, palm kernel oil, blackcurrent seed oil, rice bran oil, soybean oil, canola oil, corn oil, coconut oil, cotton seed oil, castor oil, olive oil, Linn oils (Neem), sesame oil, primrose oil, vegetable oil, Lipex 108 (Abitec), wheat germ oil, fish oil, rapeseed oil, sunflower oil and saffola oil. In alternative embodiments, it is contemplated that other diluents may be used, for example, diluents selected from calcium-aluminum silicates (Sipernat 106 PQ), calcium carbonate, calcium phosphate dibasic, calcium phosphate tribasic, calcium sulfate, microcrystalline cellulose, microcrystalline silicified cellulose, powdered cellulose, dextrates, dextrose, fructose, lactitol, lactose anhydrous, lactose monohydrate, lactose dihydrate, lactose trihydrate, mannitol sorbitol, starch, pregelatinized starch, sucrose, talc, xylitol, maltose maltodextrin, maltitol, silicon dioxide, HPMC and combinations thereof.

Process Example

The following method describes one of many suitable processes for producing a liquid-filled hard gel capsule formulation. To produce the capsule formulation listed in Table 1, the following steps are performed. First, the medium chain triglyceride (Captex 355) was added to a jacketed stainless steel vessel (temperature set at 35° C.) equipped with a vertical clamp mount mixer. Second, the Capmul® MCM (EP Type I) was melted at low temperature and added to the Captex® 355 with gentle mixing to the same jacketed stainless steel vessel. Third, Butylated Hydroxytoluene (BHT) is added to the solution by mixing. Fourth, the Dutasteride is solubilized in the solution of into Capmul/Captex/BHT with gentle mixing in the same container (alternatively dutasteride can be incorporated first with Capmul®MCM (EP Type I) and then it will be added to the solution of Captex® 355 and Butylated Hydroxytoluene (BHT)). Fifth, the yielded mixture is then machine encapsulated into gelatin capsule shells using a target fill weight of 275.0 mg. Sixth, the capsules are sealed by banding with an aqueous gelatin solution. The banding may contain colorants.

TABLE 1

| Components | mg/capsule | Percent By Weight |
|---|---|---|
| Dutasteride | 0.5 | 0.2 |
| Medium Chain Mono/Diglycerides (Capmul MCM ® EP) | 25.0 | 9.1 |
| Medium Chain Triglyceride (Captex ® 355) | 249.465 | 90.7 |
| Butylated Hydroxytoluene | 0.035 | 0.013 |
| Total Fill Weight | 275.0 | 100.0 |

The following method describes one of many suitable processes for producing a liquid-filled hard gel capsule formulation. To produce the capsule formulation listed in Table 1, the following steps are performed. First, the medium chain triglyceride (Captex 355) was added to a jacketed stainless steel vessel (temperature set at 35° C.) equipped with a vertical clamp mount mixer. Second, the Capmul® MCM (EP Type I) was melted at low temperature and added to the Captex® 355 with gentle mixing to the same jacketed stainless steel vessel. Third, Butylated Hydroxytoluene (BHT) is added to the solution by mixing. Fourth, the Dutasteride is solubilized in the solution of into Capmul/Captex/BHT with gentle mixing in the same container. Fifth, the yielded mixture is then machine encapsulated into gelatin capsule shells using a target fill weight of 275.0 mg. Sixth, the capsules are sealed by banding with an aqueous gelatin solution. The banding may contain colorants.

As an alternative, the liquid-filled hard gel capsule pharmaceutical formulation may also include long chain triglycerides as a substitute or in addition to the medium chain triglycerides described above Like above, this formulation may be a non-emulsified mixture comprising about 0.1 to about 5% by weight of at least one active pharmaceutical ingredient; about 50 to about 95% by weight long chain triglycerides; and about 5 to about 25% by weight medium chain mono/diglycerides, wherein the long chain triglycerides and medium chain mono/diglycerides are present at a ratio by weight of from about 10:1 to about 5:1.

Long chain triglycerides are triglyceride composition having fatty acids greater than 12 linear carbon atoms in length. As used herein, "long chain triglycerides" may include any suitable vegetable oil familiar to one of ordinary skill in the art. For example and not by way of limitation, the vegetable oils may include corn oil, canola oil, safflower oil, arachis oil, almond oil, peanut oil, palm oil, palm kernel oil, blackcurrent seed oil, rice bran oil, soybean oil, canola oil, corn oil, coconut oil, cotton seed oil, castor oil, olive oil, Linn oils (Neem), sesame oil, primrose oil, vegetable oil, Lipex 108 (Abitec), wheat germ oil, fish oil, rapeseed oil, sunflower oil and safflower oil. In an exemplary embodiment, the long chain triglyceride is corn oil.

To produce a capsule formulation comprising corn oil as listed in Table 2, the following steps are performed. First, the Corn Oil was added to a jacketed stainless steel vessel (temperature set at 35° C.) equipped with a vertical clamp mount mixer. Second, the Capmul® MCM was melted at low temperature and added to the Corn Oil with gentle mixing to the same jacketed stainless steel vessel. Third, Butylated Hydroxytoluene (BHT) is added to the solution by mixing. Fourth, the Dutasteride is solubilized in the solution of into Capmul/Corn Oil/BHT with gentle mixing in the same container. Fifth, the yielded mixture is then machine encapsulated into gelatin capsule shells using a target fill weight of 300 mg. Sixth, the capsules are sealed by banding with an aqueous gelatin solution. The banding may contain colorants.

TABLE 2

| Components | mg/capsule | Percent by weight |
|---|---|---|
| Dutasteride | 0.5 | 0.17 |
| Capmul MCM (Mono & di glyceride; Glyceryl Caprylate/Caprate) | 37.0 | 12.3 |
| Corn Oil (Triglyceride) | 262.465 | 87.5 |
| Butylatedhydroxytoluene (BHT) | 0.035 | 0.01 |
| Total Fill Weight | 300.0 | 100 |

As would be familiar to the skilled person, various administration regimens are contemplated for the drug. For example, the pharmaceutical formulations may be administered once a day or multiple times in a day.

For the purposes of describing and defining the present invention it is noted that the terms "substantially" and "about" are utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these aspects of the invention.

What is claimed is:

1. A liquid-filled hard gel capsule pharmaceutical formulation comprising a non-emulsified mixture disposed in a hard gelatin capsule shell, wherein the non-emulsified mixture comprises:
   about 0.1 to about 0.2% by weight of dutasteride,
   about 85% to about 95% by weight medium chain triglycerides,
   about 5% to about 15% by weight medium chain mono/diglycerides, and
   at least 0.1% to about 1% by weight of butylated hydroxytoluene,
wherein the medium chain triglycerides and medium chain mono/diglycerides are present at a ratio by weight of from about 10:1 to about 7:1.

2. The liquid-filled hard gel capsule pharmaceutical formulation of claim 1 further comprising tamsulosin.

3. The liquid-filled hard gel capsule pharmaceutical formulation of claim 1, wherein the medium chain mono/diglycerides comprise mono/diglycerides of caprylic/capric acid.

4. The liquid-filled hard gel capsule pharmaceutical formulation of claim 1, wherein the non-emulsified mixture is a substantially homogenous mixture.

5. A liquid-filled hard gel capsule pharmaceutical formulation comprising a non-emulsified mixture disposed in a hard gelatin capsule shell, wherein the non-emulsified mixture comprises:
   about 0.1 to about 5% by weight of dutasteride,
   about 87.5 to about 95% by weight long chain triglyceride,
   about 5 to about 12.3% by weight medium chain mono/diglycerides, and
   at least 0.1% to about 1% by weight of butylated hydroxytoluene,
wherein the long chain triglycerides and medium chain mono/diglycerides are present at a ratio by weight of from about 10:1 to about 7:1.

6. The liquid-filled hard gel capsule pharmaceutical formulation of claim 5 further comprising tamsulosin.

7. The liquid-filled hard gel capsule pharmaceutical formulation of claim 5 wherein the medium chain mono/diglycerides comprise mono/diglycerides of caprylic/capric acid.

8. The liquid-filled hard gel capsule pharmaceutical formulation of claim 5 wherein the long chain triglyceride comprises corn oil.

9. A liquid-filled hard gel capsule pharmaceutical formulation comprising a non-emulsified mixture disposed in a hard gelatin capsule shell, wherein the non-emulsified mixture comprises:
   about 0.2% by weight dutasteride;
   about 90.7% by weight medium chain triglycerides;
   about 9.1% by weight medium chain mono/diglycerides; and
   about 0.013% by weight butylated hydroxytoluene (BHT).

10. A liquid-filled hard gel capsule pharmaceutical formulation comprising a non-emulsified mixture disposed in a hard gelatin capsule shell, wherein the non-emulsified mixture comprises:
    about 0.1% to about 0.2% by weight of dutasteride,
    about 85% to about 95% by weight medium chain triglycerides,
    about 5% to about 15% by weight medium chain mono/diglycerides, and
    about 0.013% by weight of butylated hydroxytoluene,
wherein the medium chain triglycerides and medium chain mono/diglycerides are present at a ratio by weight of from about 10:1 to about 7:1.

11. A liquid-filled hard gel capsule pharmaceutical formulation comprising a non-emulsified mixture disposed in a hard gelatin capsule shell, wherein the non-emulsified mixture comprises:
    about 0.1% to about 0.2% by weight of dutasteride,
    about 85% to about 95% by weight medium chain triglycerides,
    about 5% to about 15% by weight medium chain mono/diglycerides, and
    about 0.01% by weight of butylated hydroxytoluene,
wherein the medium chain triglycerides and medium chain mono/diglycerides are present at a ratio by weight of from about 10:1 to about 7:1.

* * * * *